United States Patent
Schmidt et al.

(10) Patent No.: US 9,247,757 B2
(45) Date of Patent: Feb. 2, 2016

(54) **METHOD FOR USING A *BACILLUS SUBTILIS* STRAIN TO ENHANCE ANIMAL HEALTH**

(75) Inventors: Joseph Earl Schmidt, Davis, CA (US); Desmond Rito Jimenez, Woodland, CA (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 13/594,051

(22) Filed: Aug. 24, 2012

(65) Prior Publication Data

US 2012/0321592 A1    Dec. 20, 2012

Related U.S. Application Data

(63) Continuation of application No. 12/561,623, filed on Sep. 17, 2009, now abandoned.

(60) Provisional application No. 61/192,436, filed on Sep. 17, 2008.

(51) Int. Cl.
| | | |
|---|---|---|
| *A01N 63/00* | (2006.01) | |
| *C12N 1/20* | (2006.01) | |
| *A23K 1/18* | (2006.01) | |
| *A23K 1/00* | (2006.01) | |

(52) U.S. Cl.
CPC .............. *A23K 1/1813* (2013.01); *A23K 1/009* (2013.01); *A23K 1/184* (2013.01); *A23K 1/1826* (2013.01)

(58) Field of Classification Search
USPC ................. 424/93.46, 93.462; 435/252.5
See application file for complete search history.

(56) References Cited

U.S. PATENT DOCUMENTS

| | | |
|---|---|---|
| 4,919,936 A | 4/1990 | Iwanami et al. |
| 2004/0101525 A1 | 5/2004 | Lin et al. |
| 2007/0202088 A1 | 8/2007 | Baltzley et al. |
| 2007/0298013 A1 | 12/2007 | Altman |
| 2012/0328571 A1 | 12/2012 | Schmidt et al. |

FOREIGN PATENT DOCUMENTS

| | | |
|---|---|---|
| EP | 027699 A2 | 10/1988 |
| JP | 62-232343 A | 12/1987 |
| JP | H04166080 | 6/1992 |
| JP | 2000166583 A | 6/2000 |
| JP | 2007236286 A | 9/2007 |
| RU | 2266747 C1 | 12/2005 |
| WO | WO 98/50422 A1 | 11/1998 |
| WO | 2009037242 A2 | 3/2009 |
| WO | WO 2010/033714 A1 | 3/2010 |
| WO | WO 2011/116155 A1 | 9/2011 |

OTHER PUBLICATIONS

Yeow-Lim et al., Inhibition of Clostridium perfringens by a Novel Strain of Bacillus subtilis Isolated from the Gastrointestinal Tracts of Healthy Chickens Applied and Environmental Microbiology, Aug. 2005, p. 4185-4190.*
Fritts, C.A., et al., "Bacillus subtilis C-3102 (Calsporin) Improves Live Performance and Microbiological Status of Broiler Chickens," J. Appl. Poult. Res., (2000) pp. 149-155, vol. 9, No. 2.
Foster, J.W., et al., "Bacillus subtilis: An Avian Oral Pathogenicity and Toxicity Study in the Northern Bobwhite," Wildlife International Ltd., (1998) Easton, pp. 1-28, unpublished, Easton, Maryland, U.S.A.
Guo, X., et al., "Screening of Bacillus Strains as Potential Probiotics and Subsequent Confirmation of the in vivo Effectiveness of Bacillus subtilis MA139 in Pigs," Antoine Van Leeuwenhoek, (Jul. 4, 2006) pp. 139-146, vol. 90, No. 2.
Jiraphocakul, S., et al., "Influence of a Dried Bacillus subtilis Culture and Antibiotics on Performance and Intestinal Microflora in Turkeys," Poult Sci., (Nov. 1990) pp. 1966-1973, vol. 69, No. 11.
Kim, S., et al., "Selection and Characterization of Bacillus Probiotics for Human and Animal Feed," Abstract of the General Meeting of the American Society for Microbiology, (2001) p. 550, vol. 101.
Pan, Kangcheng, et al., "The Effects of Bacillus subtilis Additive on the Growth Performance, Carcass and Chicken Quality of the Broiler Chicken," (2005) pp. 11-14, vol. 20.
Teo, A.Y., and Tan, H.M, "Evaluation of the Performance and Intestinal Gut Microflora of Broilers Fed on Corn-Soy Diets Supplemented with Bacillus subtilis PB6 (CloSTAT)," J. Appl. Poult. Res., (2007) pp. 296-303, vol. 16, No. 3.
Zhou, Xiaohui et al., "A Brief Analysis of Action Mechanism and Application Effect of Bacillus subtilis Formulation," Feed and Animal Husbandry, (2008) pp. 61-62, vol. 5.
Bacillus subtilis strain QST 713 European Monograph, Bundesamt für Verbraucherschutz und Lebensmittelsicherheit (BVL), 2001 [retrieved on Jun. 13, 2012]. Retrieved from the Internet< URL: http://www.bvl.bund.de/SharedDocs/Downloads/04__Pflanzenschutzmittel/02__eu__berichte/Bacsub-DAR.pdf?__blob=publicationFile&v=2> Annex B, pp. 127-134.
European Search Report for EP Application No. 14163676.1 corresponding to PCT/US2009/057335, issued by the European Patent Office on Jun. 16, 2014.

(Continued)

*Primary Examiner* — Maria Leavitt
(74) *Attorney, Agent, or Firm* — Michelle L. Samonek

(57) ABSTRACT

The present invention relates to a method for enhancing the health of an animal comprising administering to the animal a composition comprising *Bacillus subtilus* QST 713 or a mutant thereof.

7 Claims, 8 Drawing Sheets

(56) References Cited

OTHER PUBLICATIONS

International Search Report and Written Opinion of the International Searching Authority, International Patent Application No. PCT/US2009/057335, issued Jan. 12, 2010, 8 pages.

International Search Report and Written Opinion of the International Searching Authority, International Patent Application No. PCT/US2011/028755, issued Jul. 5, 2011, 12 pages.

Hong, H.A., et al., "Bacillus subtilis Isolated from the Human Gastrointestinal Tract," Research in Microbiology, (2009) pp. 134-143, vol. 160.

Hong, H.A., et al., "The Use of Bacterial Spore Formers as Probiotics," FEMS Microbiology Reviews, (2005) pp. 813-835, vol. 29.

Lund, B. et al., "Efficacy of GalliPro: A Microbial Feed Additive for Broilers," Proceedings of the 15th European Symposium on poultry nutrition, BalatonfOred, Hungary, Sep. 25-29, 2005.

McLean, J., et al., "Benefits of Bacillus subtilis DSM 17299 (GalliPro) Supplementation in Chicken Diets," Proceedings of the 15th European Symposium on poultry nutrition, BalatonfOred, Hungary, Sep. 25-29, 2005.

Molnar, A.K., et al., "Influence of Bacillus subtilis on Broiler Performance," Proceedings of the 15th European Symposium on Poultry Nutrition, Balatonfüred, Hungary, Sep. 25-29, 2005.

* cited by examiner

METHOD FOR USING A *BACILLUS SUBTILIS* STRAIN TO ENHANCE ANIMAL HEALTH

CROSS-REFERENCE TO RELATED APPLICATIONS

This application claims priority to and is a continuation of U.S. patent application Ser. No. 12/561,623, filed Sep. 17, 2009, now abandoned, which in turn claims the benefit under 35 U.S.C. Section 119(e) of U.S. Provisional Patent Application No. 61/192,436, filed Sep. 17, 2008. The contents of the aforementioned patent applications are hereby incorporated by reference into the present disclosure.

FIELD OF INVENTION

The present invention relates to the field of probiotics and their ability to enhance animal health or the general physical condition of animals.

BACKGROUND OF INVENTION

The *Bacillus* genus comprises numerous endospore-forming bacteria that have myriad uses in the agricultural and animal nutrition fields, among others. Several strain of *Bacillus* are currently marketed for use as probiotics in animal feed as an alternative to antibiotics. These probiotics enhance animal health, including improving animal growth and feed efficiency, by modulating the gastrointestinal flora. Use of such probiotics has increased due to concerns about antibiotic residues in animal products for human consumption and the development of resistance to antibiotics. Work has been conducted in recent years to screen spore-forming bacteria for use as probiotics. Although various commercial products contain strains of *Bacillus subtilis, Bacillus licheniformis*, and *Bacillus coagulans*, such screening reveals that not all. *Bacillus* strains are effective feed additives.

SUMMARY OF INVENTION

The present invention provides a strain of *Bacillus subtilis* that, when administered to an animal, enhances the health of such animal. Specifically, the present invention relates to methods for enhancing the health of non-insect and non-human animals or for improving the general physical condition of such animals by feeding to such animals, in feed or drinking water (and not through gavage), compositions comprising (i) *Bacillus subtilis* QST 713, (ii) a mutant of (i), a cell-free preparation of (i) or (ii), or a metabolite of (i) or (ii). In one embodiment, the composition of the present invention comprises *Bacillus subtilis* 713 or mutants thereof and metabolites produced by the bacteria. In another embodiment, the composition comprises *Bacillus subtilis* QST713 mainly in its spore form.

In some embodiments of the present invention, the compositions are administered to animals in feed over multiple days throughout the animal's life or during particular stages or portions of the animal's life. For example, in some embodiments the compositions are administered only in a starter diet or only in a finisher diet of farm animals.

The methods of the present invention may be used to increase weight gain of an animal, to increase feed utilization efficiency, to reduce morbidity, to increase disease resistance, to increase survival rates, to increase the immune response of the animal and to maintain healthy gut microflora. In one embodiment the methods of this invention are used to assist with re-establishing a healthy balance of gut microflora after administration of a course of antibiotics tor therapeutic purposes.

In one embodiment, the composition of the present invention comprises *Bacillus subtilis* QST713 or mutants thereof and is administered to an animal at a rate of about $1 \times 10^3$ CFU/g feed or ml drinking water, or about $1 \times 10^4$ CFU/g feed or ml drinking water or about $1 \times 10^5$ CFU/g feed or ml drinking water, or about $1 \times 10^6$ CFU/g feed or ml drinking water, or about $1 \times 10^7$ CFU/g feed or ml drinking water, or about $1 \times 10^8$ CFU/a feed or ml drinking water, or about $1 \times 10^9$ CFU/a feed or ml drinking water, or about $1 \times 10^{10}$ CFU/g feed or ml drinking water, or about $1 \times 10^{11}$ CFU/g feed or ml drinking water.

In another embodiment, the compositions of the present invention are administered or led to an animal in an amount effective to decrease the growth of pathogenic bacteria in the animal gut. Such pathogenic bacteria include *Clostridia, Listeria, Salmonella, Campylobacter, Escherichia coli*, and *Vibrio*. Relatedly, the methods of the present invention may be used to decrease the amount of pathogenic bacteria shed in animal feces. The methods of the present invention may also be used to maintain or increase the growth of beneficial bacteria, such as lactic acid bacteria, in the animal gut. By decreasing pathogenic bacteria and/or increasing or maintaining beneficial bacteria, the compositions of the present invention are able to maintain an overall healthy gut microflora.

The methods of the present invention may be used for all non-human and non-insect animals. Animals that may benefit from methods of the present invention include but are not limited to birds, swine, ruminants, pets and exotic animals, zoo animals, aquatic animals, and horses, among others. In one embodiment, the animals are farm animals, which are raised for consumption or as food-producers, such as broilers and egg-producing chickens.

This invention also provides compositions that are adapted to enhancing the animal's health or improving the animal's physical condition. Thus, the compositions of the present invention may include *Bacillus subtilis* QST713 or its mutants, cell-free preparations thereof or metabolites thereof and carriers that make these compositions suitable for feeding to animals as a feed additive or as an additive for drinking water. Alternatively, the *Bacillus subtilis* QST713 or its mutants, cell-tree preparations thereof or metabolites thereof may be formulated with animal feed ingredients, including feed protein and/or teed carbohydrates. Such combinations may be in the form of pellets that are extruded through standard pelleting processes.

Compositions of the present invention also comprise combinations of *Bacillus subtilis* QST713 or its mutants, cell-tree preparations of QST713 or its mutants and metabolites of QST713 and its mutants with other probiotics and/or with prebiotics.

The present invention also encompasses a method for preparing animal feed containing a direct fed microbial comprising adding *Bacillus subtilis* QST713 spores in an amount effective to enhance animal health upon feeding to animals to standard feed components, such as carbohydrates and proteins, prior to the pelleting process.

DETAILED DESCRIPTION OF INVENTION

Figure 1:
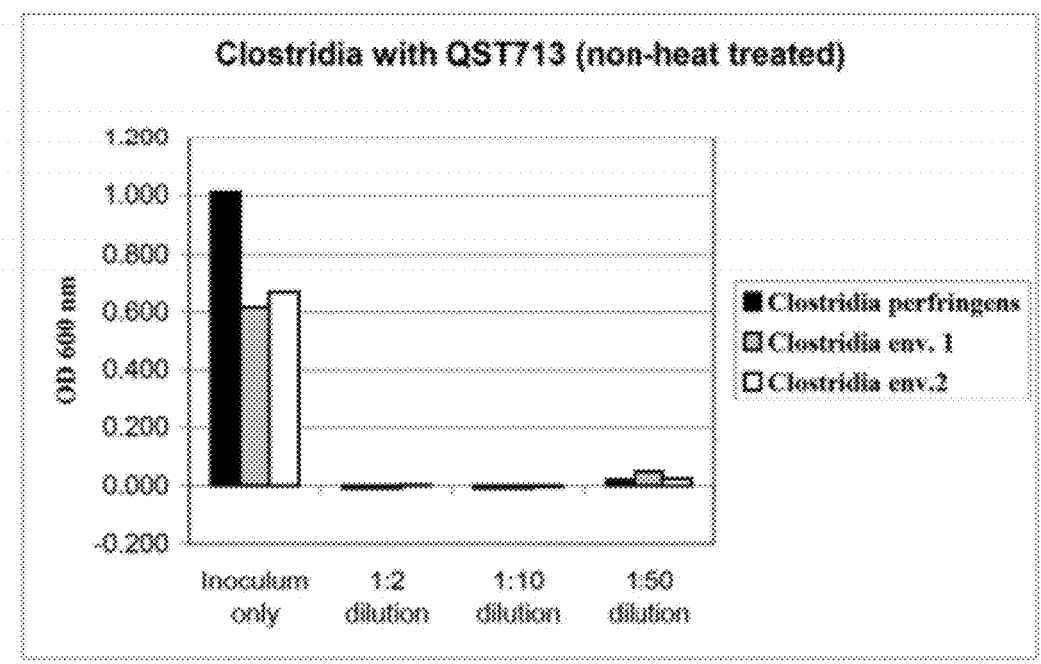
FIG. 1 shows results of a test of a cell-free preparation of *Bacillus subtilis* QST713 for efficacy against various isolates oil *Clostridia*.
Figure 2:
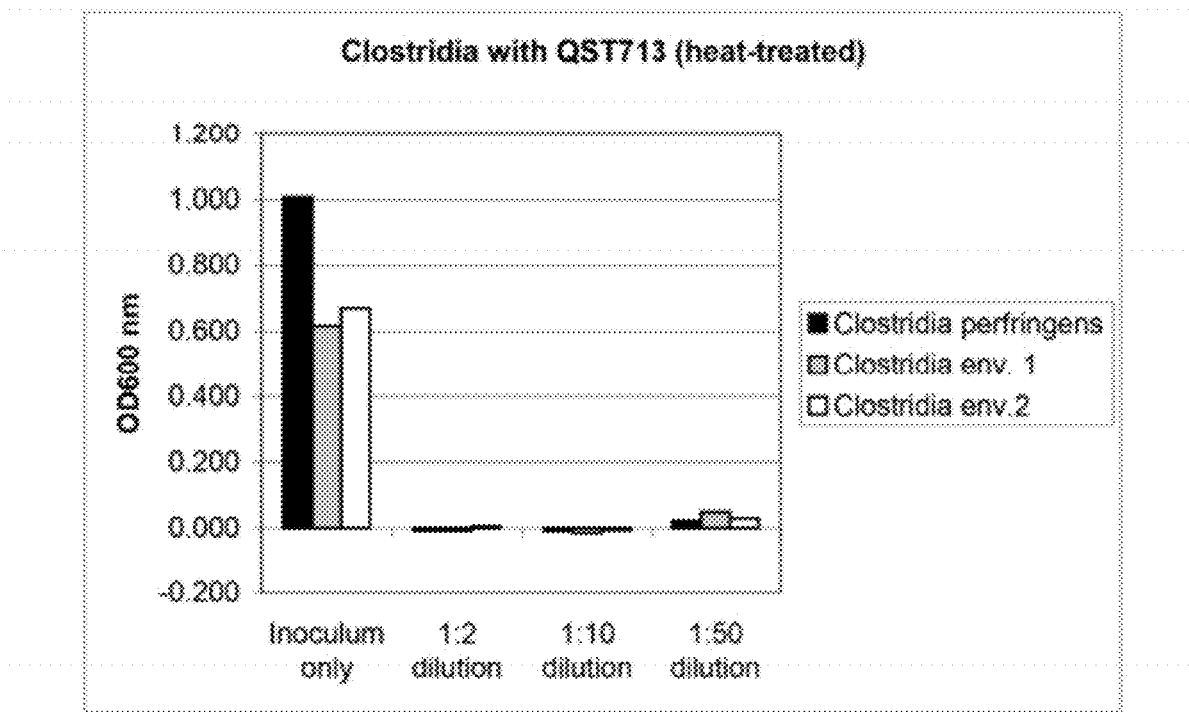
FIG. 2 represents results of a test of a heat-treated cell-free preparation of *Bacillus subtilis* QST713 for efficacy against various isolates of *Clostridia*.
Figure 3:
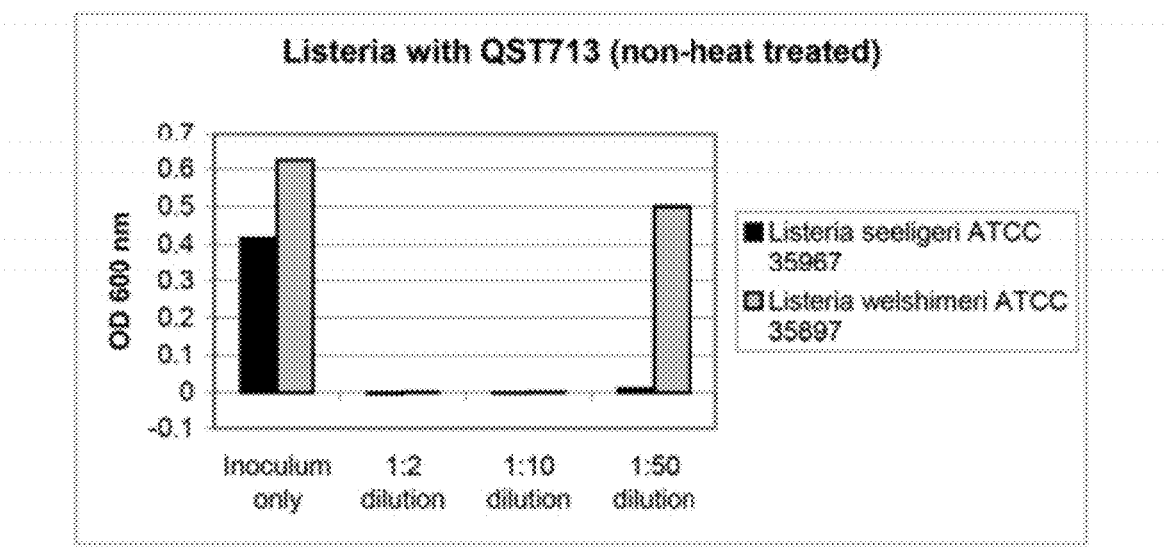
FIG. 3 shows results of a test of a cell-free preparation of *Bacillus subtilis* QST713 for efficacy against various isolates of *Listeria*.
Figure 4:
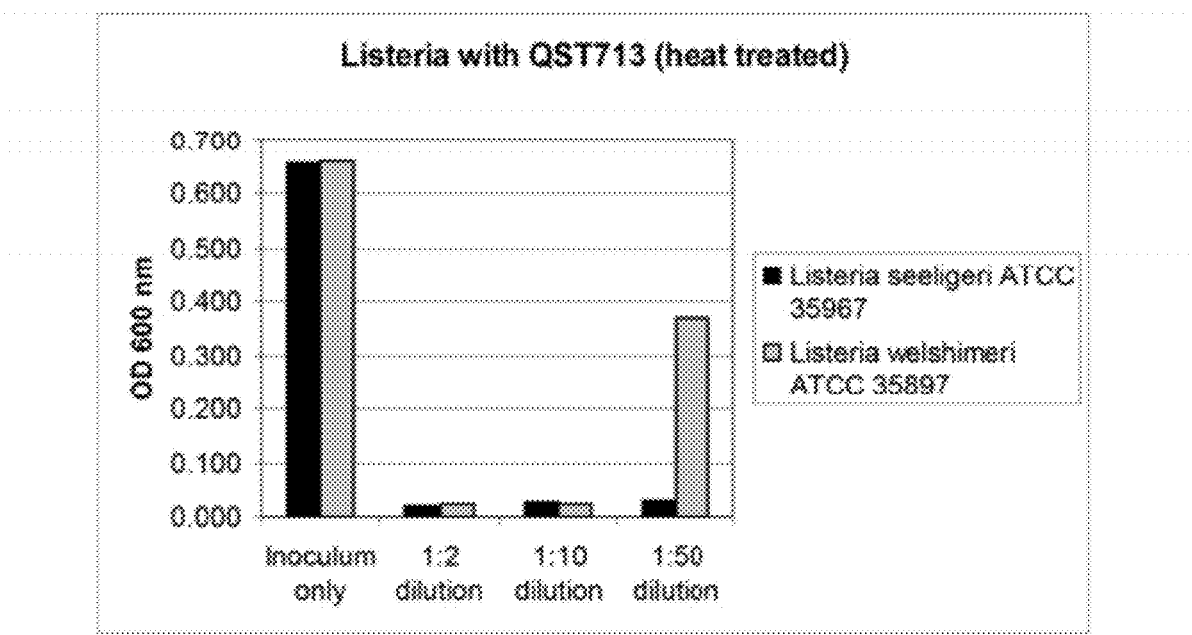
FIG. 4 represents results of a test of a heat-treated cell-free preparation of *Bacillus subtilis* QST713 for efficacy against various isolates of *Listeria*.
Figure 5:
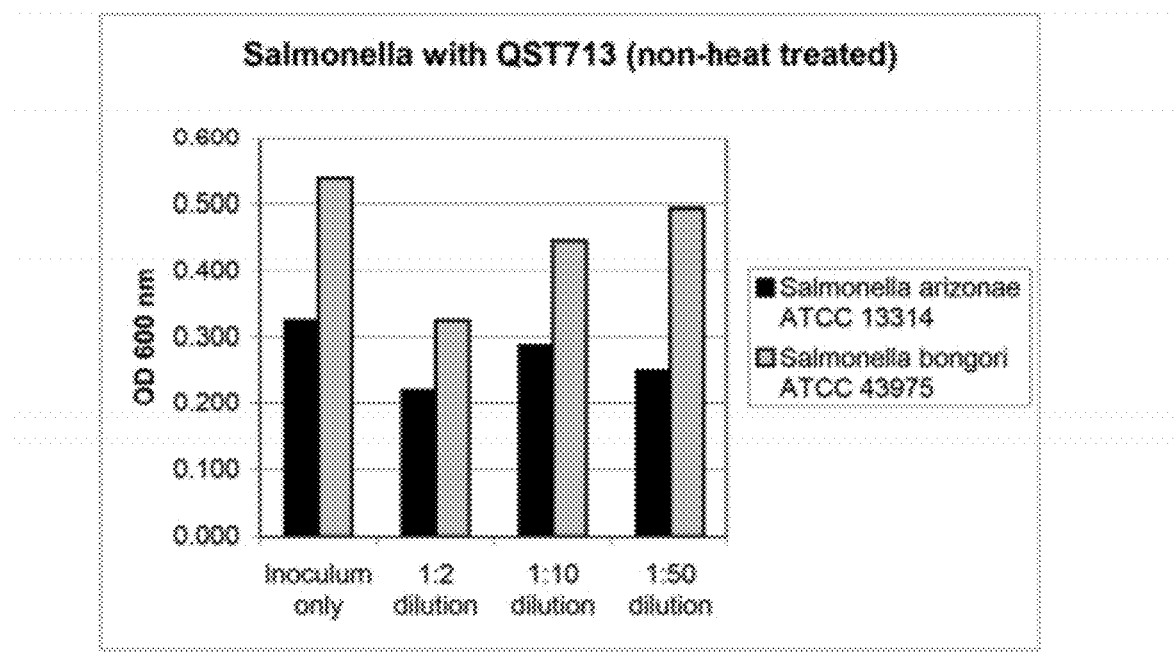
FIG. 5 shows results of a test, of a ceil-free preparation of *Bacillus subtilis* QST713 for efficacy against various isolates of *Salmonella*.
Figure 6:
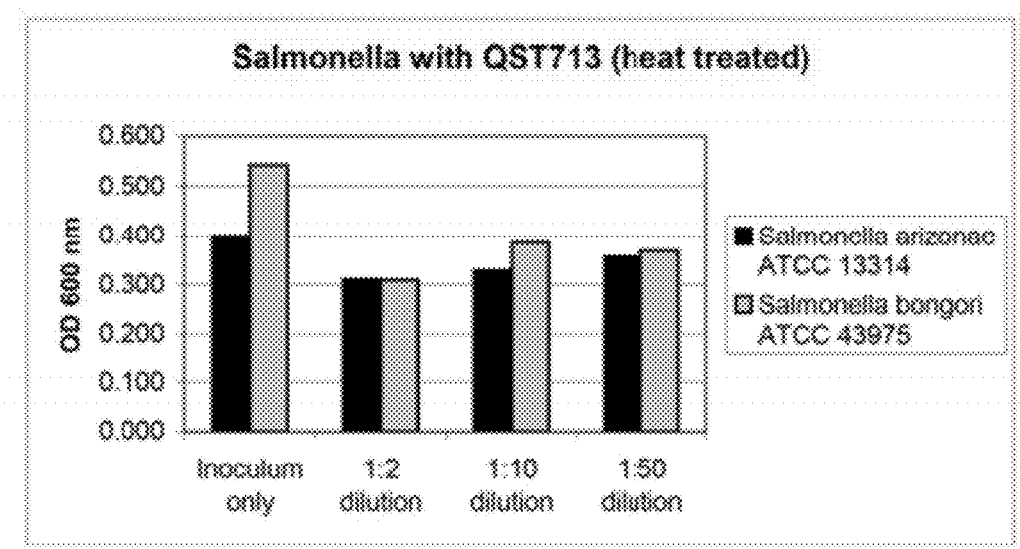
FIG. 6 represents results of a test of a heat-treated cell-free preparation of *Bacillus subtilis* QST713 for efficacy against various isolates of *Salmonella*.

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed, inventions, or that any publication specifically or implicitly referenced is prior art.

The present invention relates to a novel use of *Bacillus subtilis* strain QST 713 and/or its metabolites that are effective to enhance animal health as a probiotic. Probiotics are used in animal health applications in order to maintain healthy gut microflora, including a reduction in detrimental bacteria such as *Clostridia* and *Campylobacter* and an increase in beneficial bacteria such as *Lactobacillus* spp. and *Bifidobacterium*. Probiotics are well-suited to maintaining a healthy balance between pathogenic and beneficial bacteria because, unlike antibiotics, they do not destroy bacteria indiscriminately nor do they lead to antibiotic resistant strains of pathogenic bacteria. There are many mechanisms by which probiotics are thought to maintain healthy gut microflora: competitive exclusion of pathogenic bacteria, redaction of pathogenic bacteria through production of antimicrobial substances, enhancing growth and viability of beneficial gut microflora, and stimulating a systemic immune response in the animal.

The present invention encompasses a method for enhancing animal health by administering to an animal a composition comprising (i) *Bacillus subtilis* QST713, (ii) mutants of *Bacillus subtilis* QST713, (iii) cell-free preparations of (i) or (ii), or (iv) metabolites of (i) or (ii).

*Bacillus subtilis* QST713, its mutants, its supernatants, and its lipopeptide metabolites, and methods for their use to control plant pathogens and insects are fully described in U.S. Pat. Nos. 6,060,051, 6,103,228, 6,291,426, 6,417,163, and 6,638,910. In these patents, the strain is referred to as AQ713. *Bacillus subtilis* QST713 has been deposited with the NRRL on May 7, 1997 under the provisions of the Budapest Treaty on the International Recognition of the Deposit of Microorganisms for the Purpose of Patent Procedure under Accession Number B21661. Any references in this specification to QST713 refer to *Bacillus subtilis* QST713.

The *Bacillus subtilis* QST713 strain has certain properties, which, surprisingly, have been found to make the strain well-suited for enhancing animal health. Spores of QST713 are viable at low pHs and cells of QST713 grow (given conducive nutrient conditions) at pHs as low as 4.5. In addition, as described in Examples 8 and 4, respectively, below, QST713 is able to grow in high salt conditions for at least ten days and can survive the high temperatures necessary for pelleting animal feed. QST713 also has the ability to aggregate, or swarm, as shown in Example 2, thereby outcompeting and reducing pathogenic bacteria. Without wishing to be limited by any particular theory, it is thought that *Bacillus subtilis* QST713 enhances animal health by a multifaceted mode of action, including producing antibacterial metabolites and competing with pathogens by using more nutrients and attachment spaces than the pathogens, thereby preventing effective establishment of pathogenic bacteria in the gut.

In one aspect of the invention, compositions administered to animals comprise mutants of *Bacillus subtilis* QST713 having all the identifying characteristics of QST713. Such mutants may have DNA sequence identity to QST713 of at least about 95%, at least about 96%, at least about 97%, at least about 98%, or at least about 99%. In some embodiments, mutants are spontaneous mutants. The terra spontaneous mutant refers to mutants that arise from QST713 without the intentional use of mutagens. Such spontaneous mutants may be obtained by classical methods, such as growing the *Bacillus subtilis* strain in the presence of a certain antibiotic to which the parent is susceptible and testing any resistant mutants for improved biological activity or, in this application, improved ability to enhance one or more of the indicia of animal health described below. Other methods for identifying spontaneous mutants will be known to those of ordinary skill in the art.

All references in this application to *Bacillus subtilis* QST713 or its mutants refer to bacteria that have been isolated from nature and are grown by humans, for example, in the laboratory or under industrial conditions.

*Bacillus subtilis* QST713 cells may be present in the compositions of the present invention as spores (which are dormant), as vegetative cells (which are growing), as transition state cells (which are transitioning from growth phase to sporulation phase) or as a combination of all of these types of cells. In some embodiments, the composition comprises mainly spores.

Metabolites of QST713 or its mutants include lipopeptides, such as iturins, surfactins, plipastatins, and agrastatins and other compounds with antibacterial properties. Lipopeptide metabolites of QST713 are described in detail in U.S. Pat. Nos. 6,291,426 and 6,638,910.

Compositions of the present invention can be obtained by culturing *Bacillus subtilis* QST713 or its mutants according to methods well known in the art, including by using the media and other methods described in U.S. Pat. No. 6,060,051. Conventional large-scale microbial culture processes include submerged fermentation, solid state fermentation, or liquid surface culture. Towards the end of fermentation, as nutrients are depleted, *Bacillus subtilis* QST713 cells begin the transition from growth phase to sporulation phase, such that the final product of fermentation is largely spores, metabolites and residual fermentation medium. Sporulation is part of the natural life cycle of this *Bacillus subtilis* and is generally initiated by the cell in response to nutrient limitation. Fermentation is configured to obtain high levels of colony forming units of *Bacillus subtilis* QST713 and to promote sporulation. The bacterial cells, spores and metabolites in culture media resulting from fermentation may be used directly or concentrated by conventional industrial methods, such as centrifugation, tangential-flow filtration, depth filtration, and evaporation, in some embodiments, the concentrated fermentation broth is washed, for example via a diafiltration process, to remove residual fermentation broth and metabolites.

The fermentation broth or broth concentrate can be dried with or without the addition of carriers using conventional drying processes or methods such as spray drying, freeze drying, tray drying, fluidized-bed drying, drum drying, or evaporation. The resulting dry products may be further processed, such as by milling or granulation, to achieve a specific particle size or physical format. Carriers, described below, may also be added post-drying.

Cell-free preparations of fermentation broth of QST713 can be obtained by any means known in the art, such as extraction, centrifugation and/or filtration of fermentation broth. Those of skill in the art will appreciate that so-called cell-free preparations may not be devoid of cells but rather are largely cell-free or essentially cell-free, depending on the technique used (e.g., speed of centrifugation) to remove the cells. The resulting cell-free preparation may be dried and/or formulated with components that aid in its administration to animals. Concentration methods and drying techniques described above for fermentation broth are also applicable to cell-free preparations.

Metabolites of QST713 can be obtained according to the methods set forth in U.S. Pat. No. 6,060,051. The term "metabolites" as used herein may refer to semi-pure and pure or essentially pure metabolites, or to metabolites that have not been separated from *Bacillus subtilis* QST713. The lipopeptides and other bacteriacidal metabolites of QST713 are between 600 kilodaltons and 100 daltons. Therefore, in some embodiments, after a cell-free preparation is made by centrifugation of fermentation broth of QST713, the metabolites may be purified by size exclusion filtration that groups metabolites into different fractions based on molecular weight cut-off, such as molecular weight of less than 600 kDa, less than 500 kDa, less than 400 kDa and so on. Concentration methods and drying techniques described above for formulation of fermentation broth are also applicable to metabolites.

Compositions of the present invention may include carriers, which are inert formulation ingredients added to compositions comprising cells, cell-free preparations or metabolites to improve recovery, efficacy, or physical properties and/or to aid in packaging and administration. Such carriers may be added individually or in combination, in some embodiments, the carriers are anti-caking agents, anti-oxidation agents, bulking agents, and/or protectants. Examples of useful carriers include polysaccharides (starches, maltodextrins, methylcelluloses, proteins, such as whey protein, peptides, gums), sugars (lactose, trehalose, sucrose), lipids (lecithin, vegetable oils, mineral oils), salts (sodium chloride, calcium carbonate, sodium citrate), and silicates (clays, amorphous silica, fumed/precipitated silicas, silicate salts). Suitable carriers for animal feed additives are set forth in the American Feed Control Officials, Inc's Official Publication, which publishes annually. See, for example Official Publication of American Feed Control Officials, Sharon Krebs, editor, 2006 edition, ISBN 1-878341-18-9. In some embodiments, the earners are added after concentrating fermentation broth and during and/or after drying.

In embodiments in which the compositions are formulated as feed additives, the concentration on a weight by weight basis (w/w) of (i) *Bacillus subtilis* QST713 or its mutants, (ii) cell-free preparations of QST713 or its mutants, (iii) metabolites of QST713 or its mutants or (iv) combinations of cells and metabolites in the formulated composition may be about 5%, about 6%, about 7%, about 8%, about 9%, about 10%, about 11%, about 12%, about 13%, about 14%, about 15%, about 16%, about 17% about 18%, about 19%, about 20% about 25%, about 30%, about, 35%, about 40%, about 45%, about 50%, about 55%, about 60%, about 65%, about 70%, about 75%, about 80%, about 85%, about 90%, or about 95%. In some embodiments, for example, where the concentrated formulation broth has been washed and dried without heat, such as via freeze drying, the concentration of *Bacillus subtilis* QST 713 or its mutants in the final composition may be from about 90% to about 100%.

The compositions of the present invention may be administered/fed to non-insect and non-human animals to improve animal health or the general overall physical, condition of such animals. The compositions can be administered both for therapeutic and non-therapeutic applications. An effective amount of a composition is an amount effective to enhance the health of an animal in comparison to an animal that has not been administered the composition but otherwise has been administered the same diet (including feed and other compounds) as has the animal receiving the compositions of the present invention. Indicia of enhanced health include one or more of the following: increase in weight gain, which may include an increase in weight of a specific part of the animal or an increase in overall weight; maintenance of gut microflora; increase in feed utilization efficiency; reduction in risk of mortality; increase in disease resistance; reduction in morbidity; increase in immune response; decrease in occurrence of diarrhea, increase in productivity; and/or reduction of pathogen shedding. Thus, in line with the above, embodiments of the present application are directed to non-therapeutic methods such as increasing the weight of the animal, the maintenance of gut microflora, or an increase in feed utilization efficiency by administering/feeding to the animal a composition comprising *Bacillus subtilis* QST 713, a mutant of *Bacillus subtilis* QST 713, a cell-free preparation derived from *Bacillus subtilis* QST713 or its mutant, or metabolites of QST713 or its mutants.

In some embodiments in which the compositions of the present invention are administered/fed to farm animals, the compositions are administered in order to improve growth performance of the farm animal. As used herein, improvements to growth performance refer to increased growth (weight or length) and/or feed utilization, efficiency and/or decreased mortality/increased survival rate compared to animals that have not been administered the compositions of the present invention. In one aspect of this invention, weight increases of between about 1% and about 20%, or between about 1% and about 15%, or between about 1% and about 9% are achieved. The method of the present invention also may increase feed utilization efficiency in animals as compared to animals to which the compositions of the present invention have not been, administered. Feed efficiency is typically evaluated using the feed conversion ratio, which is the ratio of feed consumption to weight gain. A reduction of this ratio relates to increased, feed efficiency. Feed efficiency may be improved by between about 1% and 15%, between about 2% and about 10% and between about 3% and about 8%. The methods of the present invention may also reduce mortality. Survival rate improvements of between about 1% and about 20%, or between about 2% and 17% or between about 4% and about 13% or between about 5% and about 10% may be achieved. Increased growth, feed efficiency improvements and decreased mortality may be determined individually compared to averages known in the animal husbandry field or by comparing averages of growth performance data from a group of farm animals of about the same age, typically raised together and/or under similar conditions, some of which do not receive the compositions of the present invention.

Maintenance of gut microflora refers to decreasing (by killing or inhibiting the growth of) harmful, disease-causing microorganisms of public health concern and/or increasing beneficial bacteria, such as Lactobacilli and Bifidobacteria, as compared to an animal to which the methods of this invention have not been applied. Without wishing to be bound by any particular theory, it is thought that increases to beneficial bacteria may be caused by stimulating growth of such bacteria or simply by selectively decreasing pathogenic bacteria, thereby giving the beneficial bacteria more space to grow and to attach to the gut wall. Harmful, disease-causing bacteria that may be decreased by the methods of this invention include *Clostridia* spp. (such as *perfringens* and *dificile*), *Listeria* spp. (such as *moncytogenes, seeligeri* and *welshimeri*), *Salmonella* spp. (such as enterica, arizonae, typhirium, enteritidis and bonglori), *E. coli, Enterococcus* spp. (such as *faecalis* and *faecium*), *Campylobacter, Aeromonas* spp., *Staphylococcus aureus*, and *Vibrio* spp. In some embodiments, harmful, disease-causing microorganisms may be reduced by about 0.5 log, about 1 log, about 2 log, about 3 log, about 4 log, or about 5 log.

The above pathogenic bacteria lead to various diseases in animals. For example, in poultry, feed contaminated with *Clostridium perfringens* has been implicated in outbreaks of necrotic enteritis (or necrotic lesions in the gut wall) in chicken. Interestingly, although this bacteria is commonly found in the intestinal tract of chickens, it does not always result in necrotic enteritis, although increased levels have been linked to the disease. Reduction of this pathogen through use of a probiotic results in enhanced health and weight gain, as shown in the examples, below. Thus, control of these bacteria by decreasing their ability to grow in the gut reduces incidence of disease caused by such bacteria. Table 1, below, shows various microorganisms and the diseases or conditions to which they are linked.

TABLE 1

| Organism | Disease and/or Affected Animal |
| --- | --- |
| *Mycoplasma gallisepticum* | pulmonary disease in poultry |
| *Mycoplama synoviae* | joint and pulmonary disease in poultry |
| *Pasterella multocida* | fowl colera |
| *Staphylococcus aureus* | common secondary pathogen for poultry |
| *Aspergillus fumigatus* | poultry, especially turkey, respiratory pathogen |
| *Avibacterium paraglaainarum* | chicken coryza |
| *Bordetella avium* | turkey |
| *Salmonella arizonae* | turkey coryza |
| *Salmonella typhimurium* | fowl typhoid |
| *Pseudomonus aeruginosa* | common secondary pathogen for poultry |
| *E. coli* O18 or O45 k88positive | weanling diarrhea (pigs) |
| *Brachyspira hyodysenteria* | swine dysentery |
| *Lawsonia intracellularis* | ilieitis (pigs) |
| *Bordetella bronchiseptica* | atrophic rhinitis (pigs) |
| *Erysipelothrix rhusiopathiae* | ersipelas (pigs) |

Maintenance of healthy gut microflora and, in particular, reduction of one or more of the above-described detrimental bacteria, also causes a reduction in pathogen shedding through animal feces. Pathogen quantities may be determined by several methods known to those of skill in the art, including analyzing pathogen shed in animal feces or by sacrificing animals during studies and analyzing the populations of bacteria (beneficial and pathogenic) in their gut.

The methods of the present invention may also be used to restore normal intestinal balance after administration of therapeutic amounts of antibiotics by inhibiting growth of pathogenic bacteria and/or increasing or maintaining growth of beneficial bacteria. The term "therapeutic amount" refers to an amount sufficient to ameliorate or reverse a disease state in an animal.

Increased productivity obtained through the methods of the present invention refers to any of the following: production of more or higher quality eggs, milk or meat or increased production of weaned offspring.

The methods of the present invention may be applied to any animal, including vertebrates, such as mammals and aquatic animals, and crustaceans, such as shrimp, but excluding insects and humans. Mammals that may be treated with the composition of the present invention include farm animals; animals used for sports, recreation or for work, such as horses, including race horses; domestic household pets, including clogs, cats, birds and exotics; and zoo animals. Farm animals refer to animals raised for consumption or as food-producers. In one embodiment the method is applied to monogastric animals such as poultry and game birds. Poultry may include chicken, turkey, duck, geese, guinea fowl and ratite, such as ostrich and emu. Game birds may include quail, chukkar, pheasant, grouse, Cornish hens, and partridge. Chicken refers to meat-bearing chicken, which encompass chickens which are raised for slaughter, which are also called broilers, and egg-producing chickens, which are those that are used to produce eggs for human consumption. In another embodiment, the method may be applied to mammals such as swine. In yet another embodiment the method may be applied to polygastric animals, such as cattle, goat and sheep, also referred to herein as ruminants. In one embodiment, the compositions of this invention may be fed to preruminants to enhance their health and, in particular, to decrease the incidence of diarrhea in these animals. Preruminants are ruminants, including calves, ranging in age from birth to about twelve weeks. The compositions of the present invention may be administered to preruminants in conjunction with milk replacers. Milk replacers refer to formulated feed intended to replace colostrum during milk feeding stages of the preruminant.

In one aspect, the compositions of the present invention are feed additives that are added to the subject animal's feed or drinking water prior to feeding. In such case, the compositions may be formulated with a carrier, such as calcium carbonate or whey protein, as described above. In one aspect of the invention, such carrier is hydrophobic.

In another aspect, compositions comprising *Bacillus subtilis* QST713, its mutants, cell-free preparations of QST713 and its mutants, and metabolites of QST713 and its mutants can be formulated in combination with animal feed ingredients needed to promote and maintain growth of an animal. Such animal feed ingredients may include one or more of the following: protein, carbohydrate, fats, vitamins, minerals, coccidiostats, acid-based products and/or medicines, such as antibiotics. In some embodiments, carriers, such as those described above, will also be present. Protein and carbohydrates needed to promote and maintain growth shall be referred to as feed protein and feed carbohydrate to distinguish them from any residual proteins and/or carbohydrates that may remain from the bacterial fermentation process.

In another aspect, compositions of the present invention comprising *Bacillus subtilis* QST713, its mutants, cell-free preparations of QST713 and its mutants and metabolites of QST713 and its mutants may further include other probiotics, such as other species and strains of *Bacillus* that are fed to animals to enhance animal health or to improve the general physical condition of the animal. Exemplary strains include *Bacillus subtilis* PB6 (as described in U.S. Pat. No. 7,247,299 and deposited as ATCC Accession No. PTA-6737), which is sold by Kemin under the trademark CLOSTAT® or *Bacillus subtilis* C-3102 (as described in U.S. Pat. No. 4,919,936 and deposited as FERM BP-1096 with the Fermentation Research Institute, Agency of Industrial Science and Technology, in Japan), sold by Calpis as CALSPORIN®, or a mixture of *Bacillus licheniformis* and *Bacillus subtilis* spores sold by Chr. Hansen under the trademark BIOPLUS2B®, *Bacillus coagulans*, including those strains described in U.S. Pat. No. 6,849,256, *Bacillus licheniformis, Bacillus lentus, Bacillus pumilus, Bacillus laterosporus*, and *Bacillus alevi*. Other non-*Bacillus* probiotics, such as *Saccharamyces cerevisiae*, may also be used in compositions of the present invention. If such other probiotics are not formulated as part of the compositions of the present invention, they may be administered with (either at the same time or at different times) the compositions of the present invention.

In another aspect, the compositions of the present invention may include or be administered with (either at the same time or at different times) enzymes that aid in digestion of feed, such as amylase, glucanase, glucoamylase, cellulase, xylanase, glucanase, amylase and pectinase; immune modulators, such as antibodies, cytokines, spray-dried plasma; interleukins, interferons; and/or oligosaccharides, such as fructooligosaccharides, mannanoligosaccharides, galactooligosaccharides, inulin, oligofructose enriched inulin, tagatose, and polydextrose.

In embodiments in which the compositions comprise QST713 or its mutants, the bacteria should be added to feed or drinking water and fed to animals in an amount that is effective to enhance the animals' health. In one embodiment, it can be added at an inclusion rate of from about $1 \times 10^4$ CFU *Bacillus subtilis* per gram feed or ml drinking water to about $1 \times 10^{10}$ *Bacillus subtilis* per gram feed or ml drinking water. In another embodiment from about $1 \times 10^5$ CFU *Bacillus subtilis* per gram feed or ml drinking water to about $1 \times 10^9$ *Bacillus subtilis* per gram feed or ml drinking water should be administered. In yet another from about $1 \times 10^5$ CFU *Bacillus subtilis* per gram feed or ml drinking water to about $1 \times 10^9$ *Bacillus subtilis* per gram feed or ml drinking water should be administered. In yet another from about $1 \times 10^6$ CFU *Bacillus subtilis* per gram feed or ml drinking water to about $1 \times 10^8$ *Bacillus subtilis* per gram feed or ml drinking water should be administered. In some embodiments the inclusion rate is about $1 \times 10^3$ CFU *Bacillus subtilis* per gram feed or ml drinking water, or about $1 \times 10^4$ or about $1 \times 10^5$ or about 133 $10^6$ or about $1 \times 10^7$ or about $1 \times 10^8$ or about $1 \times 10^9$ or about $1 \times 10^{10}$ or about $1 \times 10^{11}$ CFU *Bacillus subtilis* per gram feed or ml drinking water. In embodiments in which compositions containing QST713 or its mutants are provided as feed additives, such compositions should have a CFU count that allows for dilution to the above-described ranges upon addition to the animal feed or drinking water.

Compositions comprising *Bacillus subtilis* QST713 or its mutants, cell-free preparations thereof, or metabolites thereof, can be added to animal feed prior to the pelleting process, such that the composition used in the above-described method forms part of animal feed pellets. In this aspect, if bacterial cells are used in the composition they are typically added in spore form to other components of the animal feed prior to the pelleting process. Standard pelleting processes known to those of skill in the art may be used, including extrusion processing of dry or semi-moist feeds. In some embodiments the pelleting process involves temperatures of at least about 65° C. In others, pelleting temperatures are between about 65° C. and about 120° C. In still others, pelleting temperatures are between about 80° C. and about 100° C. In yet others, the pelleting temperature is about 60° C., about 65° C., about 70° C., about 75° C., about 80° C., about 85° C., about 90° C. or about 100° C.

The compositions of the present invention can also be administered orally as a pharmaceutical in combination with a pharmaceutically acceptable carrier. Optimal dosage levels for various animals can easily be determined by those skilled in the art, by evaluating, among other things, the composition's ability to (i) inhibit or reduce pathogenic bacteria in the gut at various doses, (ii) increase or maintain levels of beneficial bacteria and/or (ii) enhance animal health at various doses.

For aquatic animals, including salmon, trout, shrimp and ornamental fish, in one embodiment, the compositions of the present invention may be added to fish rearing waters (rather than or in addition to fish feed) in an amount effective to enhance the health of the fish. Such effective amounts can be between about $10^4$ and about $10^{10}$ CFU *Bacillus subtilis* QST713 per ml of rearing water, or in another embodiment between about $10^5$ and about $10^9$ CFU *Bacillus subtilis* QST713 per ml of rearing water, or in yet another embodiment between about $10^6$ and about $10^8$ CFU *Bacillus subtilis* QST713 per ml of rearing water.

The following examples are given for purely illustrative and non-limiting purposes of the present invention.

EXAMPLES

Example 1

In Vitro Studies of Efficacy of QST713 Cell-Free Preparations Against Animal Pathogens Cell-free preparations of QST713 were tested for antimicrobial activity against *Clostridia* (*Clostridia perfringens* ATCC13124 and two environmental isolates of *Clostridia perfringens*); *Listeria* (*Listeria moncytogenes* ATCC 19116 and 19111, *Listeria seeligeri* ATCC 35968 and *Listeria welshimeri* ATCC 35897); *Salmonella* (*Salmonella enterica* ATCC 10398, *Salmonella arizonae* ATCC 13314 and *Salmonella bongori* ATCC 43975); and *E. coli* using Kirby-Bauer and minimal inhibitory concentration (MIC) techniques.

Cell-free preparations were prepared by growing QST713 in media corresponding to media in which the target pathogen was grown, as shown in Table 1, below, centrifuging the culture for 15 minutes at 3000 rpm at 23 C and filtering it through a 0.45 µm Nalgene filter unit. To test for heat stability, a portion of the cell-free preparation was heated to 50° C. for one hour before each of the Kirby-Bauer and MIC tests

TABLE 2

| Genus | Species/ATCC | Growth Media | Conditions for Growth |
|---|---|---|---|
| *Clostridia* | *Perfringens* ATCC 13124 | Reinforced Clostridial Medium (Oxoid Cat. No. CM0149). | Overnight growth in the AnaeroPak jar as above with 1 sachet of MGC Anaero-Indicator (Remel Cat. |

TABLE 2-continued

| Genus | Species/ATCC | Growth Media | Conditions for Growth |
|---|---|---|---|
| Clostridia | Perfringens environmental isolate | Same as above | No. 68-3001) Same as above |
| Clostridia | Perfringens environmental isolate | Same as above | Same as above |
| Listeria | monocytogenes ATCC 19116 | Brain heart infusion broth | Overnight at 37° C. |
| Listeria | monocytogenes ATCC 19111 | Same as above | Same as above |
| Listeria | seeligeri ATCC 35968 | Same as above | Same as above |
| Listeria | welshimeri ATCC 35897 | Same as above | Same as above |
| Salmonella | enterica ATCC 10398 | Trypticase Soy Broth | Same as above |
| Salmonella | arizonae ATCC 13314 | Same as above | Same as above |
| Salmonella | bongori ATCC 43975 | Same as above | Same as above |

In the Kirby-Bauer experiments, 2 mm sterile filter paper disks were immersed in QST713 supernatant and air-dried under sterile conditions. These disks were then placed on lawns of the target pathogen, incubated overnight and zones of inhibition measured. Zones of inhibition were observed for the *Clostridia* and *Listeria* targets.

In the MIC technique, wells of microtiter plates were inoculated with 75 ul of each target pathogen, diluted to $1\times10^5$. The above-described cell-free preparation was added to each well at final, dilutions of 1:2, 1:10 and 1:50. Plates were incubated overnight at 37° C. and OD600 and read with a Wallach microtitre reader. The cell-free preparation (both heat-treated and non-heat treated) was significantly effective against the *Clostridia* and *Listeria* targets and inhibited growth of *Salmonella* and *E. coli*, although no zones of inhibition were observed for these last two pathogens on Kirby-Bauer plates. Data for *Clostridia*, *Listeria* and *Salmonella* are shown in FIGS. 1-6.

Example 2

In Vitro Studies of Efficacy of QST713 Against Various Bacteria

Figure 7:
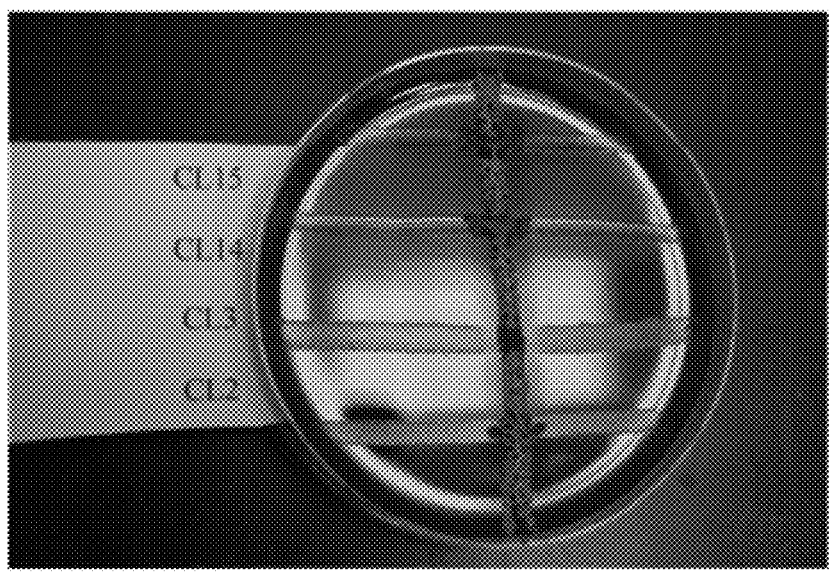
FIG. 7 shows agar plates on which *Bacillus subtilis* QST713 (vertical) and various isolates of *Clostridium perfringens* (horizontal) were cross streaked in order to test efficacy of QST713 against the pathogens.
Figure 8:
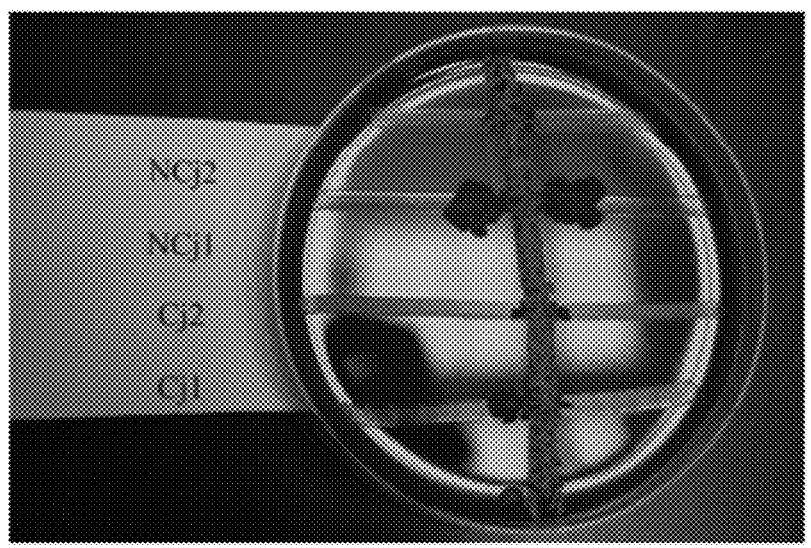
FIG. 8 shows agar plates on which *Bacillus subtilis* QST713 (vertical) and various isolates of *Campylobacter jejuni* (horizontal) were cross streaked in order to test efficacy of QST713 against the pathogens.

A powder formulation of *Bacillus subtilis* QST713 was tested for efficacy against various environmental isolates of the following bacteria: *Clostridium perfringens, Escherichia coli, Samonella enteritidis, Campylobacter jejuni,* and *Listeria monocytogenes*. This powder formulation was prepared, by fermenting *Bacillus subtilis* QST713, concentrating the fermentation broth, and drying, as described above in the Detailed Description of Invention. It had 14.6% concentrated, dried broth and 85.4% formulation inerts (chosen from the possibilities described above) and contained at a minimum approximately $7.3\times10^9$ CFU *Bacillus subtilis*/gram and at a maximum approximately $1\times10^{10}$ CFU *Bacillus subtilis*/gram. This formulation shall be referred to herein as Composition 1. Stock solutions of Composition 1 were prepared by adding 0.2 gram of the formulated powder to 1.8 ml of sterile distilled water, such that the solution contained roughly $1\times10^9$ CFU *Bacillus subtilis* per ml. Test organisms were streaked to trypticase soy agar with 5% sheep blood with up to four organisms streaked to a single agar plate each in a single line that bisects the agar plate. The organisms were allowed to dry overnight. Then, the inoculated plates were streaked with the suspension of formulated QST713 described above, which was swabbed perpendicular to the test organisms. The *Clostridium perfringens* and *Campylobacter jejuni* isolates were incubated in a Campy gas atmosphere (10% CO2, 5% O2, 8% N2) at 41±2 C overnight. The other isolates, which are aerobic, were incubated in 36±2 overnight without Campy gas. QST713 caused inhibition of several of the isolates of *Clostridium perfringens, Salmonella enteritidis, Campylobacter jejuni* and *Listeria monocytogenes*, although no inhibition of *E. coli*. In addition, in some cases *Bacillus subtilis* QST713 showed aggressive competitive overgrowth of the pathogenic bacteria. Results are summarized in the table below. The zones of inhibition reported in the table were measured from the edge of the *Bacillus* growth to the beginning of growth of the test organism. In addition, photographs of the *Clostridium perfringens* and *Campylobacter jejuni* plates are shown in FIGS. 7 and 8, respectively.

TABLE 3

| Culture Name | Isolate ID | Atmosphere and Temperature | Zone of inhibition (mm) | Comments |
|---|---|---|---|---|
| Clostridium perfringens | CL-2 | Campy gas, 41° C. | 0 | Slight inhibition of growth although no zone, *Bacillus* swarming |
| | CL-3 | | 3 | |
| | CL-14 | | 0 | *Bacillus* swarming |
| | CL-15 | | 0 | *Bacillus* swarming |
| Escherichia coli O157 | EC-80 | Aerobic, 36° C. | 0 | |
| | EC-81 | | 0 | |
| | EC-82 | | 0 | |
| Salmonella enteritidis | SE 27 | Aerobic, 36° C. | 0 | |
| | SE 28 | | 2 | |
| | SE 29 | | 1 | |
| | SE 03 | | 1 | |
| | SE 09 | | 1 | |
| | SE 22 | | 0 | |
| Campylobacter jejuni | Cj-1 | Campy gas, 41° C. | 1 | *Bacillus* swarming |
| | Cj-2 | | 0 | Slight inhibition of growth although no zone, *Bacillus* swarming |
| | NCj1 | | 0 | *Bacillus* swarming |
| | NCj2 | | 1 | |
| Listeria monocytogenes | LM 1 | Aerobic, 36° C. | 2 | |

Example 3

In Vivo Studies of QST713 in Broilers

Composition 1 was added to starter and finisher diets of broiler chickens and weight gain and feed efficiency observed. 252 Jumbo Cornish Cross broiler chicks were randomly separated into four groups and fed one of the diets listed below.

Basal diet only—control

Basal diet+0.05% CALSPORIN® (0.5 g/kg; $10^6$ CFU/g) (designated as CS in the table below)

Basal diet+0.05% Composition 1 (0.5 g/kg; $10^6$ CFU/g) (designated as Comp. $1$-$10^6$ in the table below)

Basal diet+0.0005% Composition 1 (0.5 mg/kg; $10^3$ CFU/g) (designated as Comp. $1$-$10^3$ in the table below)

The basal diet consisted of the following starter diet for days 1-22 and the following finisher diet for days 22-42.

TABLE 4

Ingredient composition of starter (d 1 to 21) and finisher (d 22 to 42) basal diets for broiler chickens

| Ingredient, % | Starter | Finisher |
|---|---|---|
| Corn | 45.6 | 49.2 |
| Soybean meal (48% CP) | 23.5 | 16.8 |
| Distillers dried grains | 5.0 | 5.0 |
| Corn gluten meal | 2.0 | 4.0 |
| Fish meal | 1.0 | 2.5 |
| Alfalfa meal | — | 0.5 |
| Vitamin, Mineral, Other | 22.9 | 22.0 |

The below results in Table 5 show that Composition 1 improved the weight gain of the birds at the $10^6$ CFU/g level. Feed efficiency was improved for the 21-42 day period and for the overall growth period (1-42 days). In the chart below, ADG refers to average daily gain, ADFI refers to average daily feed intake.

TABLE 5

Effect of dietary treatment on performance of broiler chickens

| Item | Control | CS | Comp. 1-$10^6$ | Comp. 1-$10^3$ |
|---|---|---|---|---|
| Body Weight, g | | | | |
| d 1 | 40.5 ± 0.43 | 40.0 ± 0.40 | 40.8 ± 0.43 | 40.7 ± 0.43 |
| d 21 | 861.8 ± 22.3 | 815.6 ± 20.3 | 880.0 ± 22.3 | 842.3 ± 22.3 |
| d 42 | 2494.4 ± 66.7 | 2469.0 ± 60.9 | 2617.0 ± 66.7 | 2460.3 ± 66.7 |
| ADG, g | | | | |
| d 1-21 | 39.8 ± 0.89 | 37.7 ± 0.81 | 39.8 ± 0.89 | 38.9 ± 0.89 |
| d 21-42 | 77.9 ± 3.18 | 77.5 ± 2.90 | 82.5 ± 3.18 | 78.3 ± 3.18 |
| d 1-42 | 58.4 ± 1.46 | 57.8 ± 1.33 | 61.3 ± 1.46 | 57.9 ± 1.46 |
| ADFI, g | | | | |
| d 1-21 | 57.3 ± 1.15 | 55.9 ± 1.05 | 59.4 ± 1.15 | 57.6 ± 1.15 |
| d 21-42 | 156.6 ± 3.56 | 158.3 ± 3.25 | 155.3 ± 3.56 | 158.7 ± 3.56 |
| d 1-42 | 105.2 ± 2.30 | 104.9 ± 2.10 | 106.6 ± 2.30 | 106.7 ± 2.30 |
| Gain:Feed, g/g | | | | |
| d 1-21 | 0.69 ± 0.015 | 0.67 ± 0.014 | 0.66 ± 0.015 | 0.67 ± 0.015 |
| d 21-42 | 0.50 ± 0.024 | 0.50 ± 0.022 | 0.52 ± 0.024 | 0.49 ± 0.024 |
| d 1-42 | 0.50 ± 0.022 | 0.51 ± 0.020 | 0.52 ± -0.022 | 0.48 ± 0.022 |
| Mortality, n | 1.2 ± 0.51 | 1.2 ± 0.46 | 1.4 ± 0.51 | 1.4 ± 0.51 |

Example 4

Stability of QST713 in Feed Pelleting Process

To determine the stability of *Bacillus subtilis* QST713 during the animal feed pelleting process, animal feed pellets containing Composition 1 were prepared and samples tested at various temperatures. Control feed contained the ingredients shown in Table 6, while experimental feed was supplemented with 8% Composition 1.

TABLE 6

| Ingredient | % |
|---|---|
| Corn | 68.94 |
| Soybean Meal | 20.40 |
| Fishmeal | 5.50 |
| Monocalcium Phosphate | 0.51 |
| Limestone | 0.58 |
| Salt | 0.33 |
| DL-Methionine | 0.31 |
| L-Lysine 98% | 0.18 |
| Poultry Vit/Min | 0.25 |
| Premix Soybean Oil | 3.00 |
| TOTAL | 100.000 |

Ingredients were mixed in a Foberg mixer at ambient temperatures and then heated to various target temperatures at which they were maintained for about 30 s before being pelleted at about 2000 lbs/hour through a 5/32"×1¼" pellet die. Ten samples were taken from ten different places throughout the mixer. Pellet samples were taken at target temperatures of 65° C., 75° C., 80° C., and 85° C. within the same 750 lb. batch.

Mixer samples were diluted and allowed to sit for five minutes to fully wet. Pellet samples were soaked for 30 minutes in phosphate buffer in order to recover QST713 cells.

Diluted samples were plated to determine colony forming units. Colony forming units decreased insignificantly from the mixer to the pelleting stages, as shown in Table 7, below.

TABLE 7

| Material | CFU/g |
|---|---|
| 8% *Bacillus* Mixer 1 | 1.98E+09 |
| 8% *Bacillus* Mixer 2 | 1.62E+09 |
| 8% *Bacillus* Mixer 3 | 1.62E+09 |
| 8% *Bacillus* Mixer 4 | 1.42E+09 |
| 8% *Bacillus* Mixer 5 | 1.73E+09 |
| 8% *Bacillus* Mixer 6 | 1.64E+09 |
| 8% *Bacillus* Mixer 7 | 1.63E+09 |
| 8% *Bacillus* Mixer 8 | 1.44E+09 |
| 8% *Bacillus* Mixer 9 | 1.72E+09 |
| 8% *Bacillus* Mixer 10 | 1.64E+09 |
| 8% *Bacillus* Pellets 85° C. | 1.56E+09 |
| 8% *Bacillus* Pellets 80° C. | 1.71E+09 |
| 8% *Bacillus* Pellets 75° C. | 1.73E+09 |
| 8% *Bacillus* Pellets 65° C. | 1.09E+09 |

Example 5

In Vivo Studies of QST713 in Swine

A trial using QST713 in feed pellet form was conducted using 750 pigs in a nursery pig setting. Composition 1 was added to feed prior to its pelletization by standard processes. Studies of CFU of QST713 before and after the standard pelletization process were consistent with the results obtained in Example 4, above, and showed that CFU of QST713 did not decrease dramatically after pelleting.

Approximate starting weight/pig was 10 lbs., and goal was for pigs to grow to approximately 40 lbs. A control treatment consisting of a standard diet without any antibiotics or *Bacillus* was fed to approximately 250 pigs. Another 250 pigs received the standard diet plus $1 \times 10^6$ CFU *Bacillus subtilis* QST713 per g of feed. A third group of 250 pigs was fed $1 \times 10^7$ CFU *Bacillus subtilis* QST713 per gram feed. The number of culled pigs in the third group was significantly reduced compared to the control group. The practice of culling involves removing less healthy or undersized pigs from feeding to be given therapeutic products or euthanized.

Example 6

In Vivo Studies of QST713 in Poultry

A trial using Composition 1 as a feed additive was conducted using broiler chickens with 50 birds per litter floor pen and 6 pens per treatment. Composition 1 was added to standard feed for poultry (not containing other probiotics or antibiotics) at a rate of 91 grams Composition 1 per ton feed (approximately $6.64 \times 10^{11}$ CFU/ton). One of the control groups and the group of birds administered feed supplemented with Composition 1 were challenged with *Clostridium perfringens* on days, 19, 20 and 21 of the study. Weight was recorded throughout the study and is shown in Table 8, below. Feed efficiency was determined and reported as the feed conversion ratio in Table 9, below. The feed conversion ratio was adjusted with the weights of dead and removed birds. On Day 22 of the study, five birds from each pen were selected, sacrificed, weighed, and examined for the degree of presence of Necrotic Enteritis (NE) lesions. The NE scoring was based on a 0 to 3 score scale, with 0 being normal and 3 being the most severe. In Tables 8 and 9, means within columns with different superscripts are significantly different (P<0.05). SEM is the standard error of the LSMEANS.

TABLE 8

Effects of dietary treatment on weight gains of broiler chickens in a *Clostridium perfringens* challenge model in litter floor pens.

| Treatments | Average weight (kg) Day 0 | Average Weight Gain (kg) | | |
|---|---|---|---|---|
| | | Days 0 to 21 | Days 0 to 42 | Days 21 to 42 |
| Control (NC) | .044 | .515$^A$ | 1.892$^A$ | 1.377$^A$ |
| Challenged Control (CP) | .044 | .469$^B$ | 1.704$^B$ | 1.235$^B$ |
| Composition 1 (CP) | .044 | .496$^{AB}$ | 1.838$^A$ | 1.342$^{AB}$ |
| SEM | .000 | .011 | .041 | .037 |
| Pr > F | .3712 | .0415 | .0049 | .0083 |

TABLE 9

Effects of dietary treatment on feed conversion and necrotic enteritis lesions of broiler chickens in a *Clostridium perfringens* challenge model in litter floor pens.

| Treatments | Feed Conversion Ratio (feed to gain ratio) | | | Necrotic Enteritis Lesion Score |
|---|---|---|---|---|
| | Days 0 to 21 | Days 0 to 42 | Days 21 to 42 | |
| Control (NC) | 1.723$^B$ | 1.943$^B$ | 2.055$^B$ | 0.17$^C$ |
| Challenged Control (CP) | 1.893$^A$ | 2.051$^A$ | 2.183$^A$ | 1.30$^A$ |
| Composition 1, CP | 1.765$^B$ | 1.964$^B$ | 2.128$^{AB}$ | 0.77$^B$ |
| SEM | .026 | .021 | .040 | .17 |
| Pr > F | .0003 | .0010 | .0490 | .0009 |

Example 7

Use of Composition 2 for Various Studies

Trials are conducted to test growth performance improvement using a second formulation of *Bacillus subtilis* QST713. This powder formulation is prepared by fermenting, concentrating the fermentation broth, drying it and washing it via a diafiltration process to remove residual fermentation medium and metabolites, all as described above, such that the composition is comprised essentially of cells—mainly spores and some vegetative cells. This composition contains 14.6% concentrated, dried, washed culture and 85.4% formulation inerts (chosen from the possibilities described above in the Detailed Description of Invention) and about $1.0 \times 10^{10}$ CFU *Bacillus subtilis*/gram and shall be referred to herein as Composition 2. Composition 2 is substituted for Composition 1 in the trials described in Examples 3-6 and results are expected to be the same as those achieved with Composition 1.

Example 8

Viability of QST713 Spores in Seawater

Composition 1 was tested to determine viability in seawater and NaCl. Artificial seawater was prepared in three concentrations; 10 ppt, 30 ppt, 50 ppt; 4 tubes of 25 ml per concentration. Nutrient Broth was prepared with three concentrations of NaCl; 1%, 3%, and 5%; 4 tubes of 25 ml per concentration. Both sea waters and nutrient broths were sterilized by autoclaving prior to inoculation. A suspension of Composition 1 was made by dissolving 0.5 g in 10 ml DI water. Aliquots (0.5 ml) of the suspension were inoculated into each of the three concentrations of sea water and broth. It was estimated that the tubes contained >$10^7$ cfu/ml (cfu=colony forming unit). Dilution bottles of 1% Nutrient Broth and 1% NaCl were prepared (99 ml per bottle) and sterilized by autoclaving. Nutrient Agar was prepared according to the manufacturer's directions; 15×100 mm plates were prepared for the plate count testing, one plate per test plus uninoculated controls.

The tubes were incubated at 28° C. in a shaking incubator, using 125 rpm, for 14 days. Samples for subculture were taken at days 0, 2, 10 days. On day 0 all tubes were tested; on days 2 and 10 only the 2 highest concentrations of seawater and NaCl were tested. Plate counts were obtained by plating 10 μl of the original tube on day 0 (=to $10^{-2}$ dilution) and 100 ul of $10^{-2}$ and $10^{-4}$ dilutions prepared in 1% Nutrient Broth/ 1% NaCl on days 2 and 10. Thus, the counts obtained were actually at the $10^{-3}$ and $10^{-5}$ level. The plates were incubated at 28° C. Colonies were observed at 24 and 48 hr.

Turbidity readings were obtained using a Spectronic 20D+ instrument, 12×75 polystyrene fraction collector tubes as cuvettes, and 660 wave length by measuring the absorbency of each sample. The test samples were made on day 0 by preparing a 1:10 dilution from each tube (0.5 ml in 4.5 ml 1% saline and on days 2 and 10 by testing 5 ml of the 24 hr subcultures of the $10^{-2}$ and $10^{-4}$ dilutions). In addition turbidity readings were obtained on the 8th day of incubation of the day 2 dilutions.

Both the plate cultures and turbidity readings indicated that the spores persisted with little or no diminishment of numbers for at least ten days.

The culture plates were read at 24 and 48 hr. At 24 hr the $10^{-3}$ plates were all confluent with bacterial growth. The $10^{-5}$ plates were lighter, but still had ~1000 colonies per plate. By 48 hrs all plates had heavy confluent growth, thus over $10^8$ cfu per ml in the original tube. This number was maintained at days 0, 2, and 10. There were no differences observed in cultures grown with a range of concentrations of seawater or NaCl. The culture of Composition 1 grew well in all ranges tested. There was no growth at any time in the uninoculated sea waters or nutrient broth with NaCl.

The turbidity tests (absorbency readings) gave similar results, but were more difficult to interpret. The original tubes could not be read directly as they were too turbid, especially at the highest concentration of seawater. A 1.10 dilution was used to obtain the day 0 reading. The day 2 and day 10 readings were on the dilutions used to inoculate the culture plates and could be taken from the dilution bottles. Since the estimated numbers on days 2 and 10 were greater than $10^8$ per ml there was little, if any, adverse affect on growth due to saline concentrations.

Composition 1 was tested in three concentrations of artificial seawater (10 ppt, 30 ppt, and 50 ppt), and three concentrations of NaCl in nutrient broth (1%, 3%, and 5%), for persistence. The probiotic grew in all concentrations and was viable for at least ten days in high numbers >$10^8$/ml. The concentration of salt in the sea water or in the broth did not affect the ability of the spores to germinate and grow.

Example 9

In Vivo Studies of QST713 in Trout

Rainbow trout of about 14 grams are divided into two groups of 20 fish each. The control group is fed standard fish feed, while the treated group receives fish feed and $1\times10^6$ CFU *Bacillus subtilis* QST713 per gram of feed. The treated group is expected to show increased body weight compared to the control group.

Example 10

In Vivo Studies in Shrimp

To determine the inhibitory action of QST713 against known pathogens of *Penaedae* and *Palaemonidae* shrimp and prawns. Compositions 1 and 2 are tested against three bacterial pathogens isolated from cultivated shrimp: *Vibrio parahaemolyticus, V. alginolyticus,* and *V. vulnificus* and a pathogenic fungus from shrimp, *Fusarium solani*. Stock solutions of Composition 1 and Composition 2 are prepared by adding 0.2 gram of the formulated powder to 1.8 ml of sterile distilled water, such that each solution contains about $1\times10^9$ CFU *Bacillus subtilis* per ml.

Condiospores from 5 day-old cultures of *Fusarium solani* grown on Sabouraud-Dextrose agar are harvested in sterile 2% NaCl. Vibrio are grown on Luria Broth medium at 37° C. Marine bacterial substrains are enriched on Mueller Hinton agar or marine broth 2216 medium at 30° C. and then cultured in tryptic soy broth (TSB), supplemented with 1-3% NaCl at 30° C. *V. parahaemolyticus* strains are selectively grown on Thiosulfate Citrate Bile Salts agar at 42° C. and then cultured on TSB supplemented with 3% NaCl at 30° C.

The test organisms, *Vibrio* and *Fusarium*, are streaked to a single supportive agar plate, each in a single line that bisects the agar plate. The organisms are allowed to dry overnight. Then, two sets of the inoculated plates are streaked with either the suspension of Composition 1 or of Composition 2 described above, which is swabbed perpendicular to the test organisms. The streaked plates are incubated in 36° C.±2 overnight. QST713 is expected to cause inhibition of several of the isolates of pathogenic *Vibrio* and *Fusarium*. In addition, in some cases *Bacillus subtilis* QST713 is expected to show aggressive competitive overgrowth of the pathogenic bacteria.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A method for enhancing the weight gain of poultry comprising:
    administering to the poultry a basal diet feed from day 1-42 comprising about $1\times10^6$ colony forming units (CFU) of *Bacillus subtilis* (*B. subtilis*) QST713 per gram of the basal diet feed (CFU/g) wherein the weight gain of the poultry is increased within a 21-42 days period compared to the weight gain of the poultry fed with the basal diet feed without the $1\times10^6$ CFU/g of *B. subtilis* QST713.

2. The method of claim 1, wherein the said administration is effective to increase survival rate of the poultry compared to an average survival rate of poultry fed with the basal diet feed without the about $1\times10^6$ CFU/g of *B. subtilis* QST713.

3. The method of claim 1 wherein the poultry is a broiler chicken.

4. The method of claim 1 wherein the poultry is an egg-producing chicken.

5. The method of claim 1, wherein the basal diet feed further comprises a carrier.

6. The method of claim 1, wherein the basal diet feed comprises proteins.

7. The method of claim 1, wherein the basal diet feed comprises carbohydrates.

* * * * *